United States Patent [19]

Thielen et al.

[11] Patent Number: 4,671,960

[45] Date of Patent: Jun. 9, 1987

[54] HERBAL REPELLENT COMPOSITION

[76] Inventors: Peter Thielen; Carol A. Thielen, both of P.O. Box 1574, Sedona, Ariz. 86336

[21] Appl. No.: 887,981

[22] Filed: Jul. 25, 1986

Related U.S. Application Data

[63] Continuation of Ser. No. 590,520, Mar. 16, 1984, abandoned.

[51] Int. Cl.⁴ ............................................. A01N 65/00
[52] U.S. Cl. ......................... 424/195.1; 424/DIG. 10; 514/876
[58] Field of Search .................... 424/195.1, DIG. 10; 514/876

[56] References Cited

U.S. PATENT DOCUMENTS 4,164,561  8/1979  Hautman ............................... 424/29
4,193,986  3/1980  Cox ....................................... 424/28

Primary Examiner—Johnnie R. Brown
Assistant Examiner—John W. Rollins, Jr.
Attorney, Agent, or Firm—Charles N. Hilke

[57] ABSTRACT

A natural flea repellent herbal composition using the dry, finely chopped solids of pennyroyal, eucalyptus, and camomile with a small amount of oil of pennyroyal, eucalyptus, and citronella for increased effect.

A method for production of a material receptical used as a pet collar.

An apparatus for the insertion of the natural flea repellent herbal composition within the material receptical.

1 Claim, 5 Drawing Figures

HERBAL REPELLENT COMPOSITION

This is a continuaion of co-pending application Ser. No. 590,520 filed on Mar. 16, 1984, now abandoned.

BACKGROUND OF THE INVENTION

1. Field of the Invention

This invention generally relates to a natural flea repellent herbal composition used in pet collars; a method for the production of pet collars; and an apparatus for insertion of the herbal composition into the material receptical.

2. Description of the Prior Art

The use of pet collars to control insects on pets is well known in the prior art. Natural compositions as insect repellents have previously been used, for example, in U.S. Pat. No. 4,193,986. This patent discloses the use of between 2 percent and 7 percent by weight active ingredients which consist of oil of pennyroyal, oil of eucalyptus, cedar oil, oil of citronella and oil of rue. However, by far the largest percentage comprises the inert vehicle which is between 93 and 98 percent by weight. No active dry herbs are used.

Previous inventions have used a loosely woven fabric tube as a flea repelling animal collar. U.S. Pat. No. 2,734,483. The use of rectangular fabric and the method of production of the pet collar is new and unique.

OBJECT OF THE INVENTION

It is an object of the invention to provide an active natural repellent herbal composition.

It is a further object to provide a non-irritating and harmless repellent.

Another further object is to simplify the method of production of pet collars.

Another object is to produce efficiently pet collars.

Another further object is to make an attractive, colorful stuffed collar for animals which looks like a bandana tied around an animal's neck.

A final object is to provide an apparatus for efficiently adding the natural flea repellent herbal composition to the pet collar.

SUMMARY OF THE INVENTION

The present invention comprises an herbal composition of approximately 98 percent by weight of a mixture in dry finely chopped, tea bag like mix of camomile, pennyroyal, and eucalyptus. Approximatel 2 percent by weight of the mixture is made from pennyroyal oil, eucalyptus oil and citronella oil.

The method used to make the material receptical for the above-mentioned herbal composition includes the step of cutting of the fabric in rectangles, sewing a long cord inside the base end of the folded fabric and stitching together the upper and lower side of the rectangular fabric. The cord then is pulled so that the fabric turns right side out with the base seam and length seam within the material receptical. The herbal composition is then added to the material receptical. After the herbal composition has filled the material receptical, the top end of the cord is stitched within the end of the material receptical. The cord is then cut in two.

The apparatus used for placing the herbal composition within the material receptical comprises a motor driven auger in a cylinder with the herbal composition feed in by a funneled hopper.

DESCRIPTION OF THE PREFERRED EMBODIMENTS

The herbal composition consists of 100% active ingredients in a dry mix form combined with a liquid or oil form. The dry mix ingredients are camomile, pennyroyal, and eucalyptus. The oil mix ingredients are pennyroyal oil, eucalyptus oil, and citronella oil.

Camomile dry mix is the foliage and flower heads from the genus anthemis.

Pennyroyal dry mix is the leaves and flowering tops of hedeoma or squaw mint. Pennyroyal oil is primarily pulegone.

Eucalyptus dry mix is the leaves of various eucalyptus species. The oil is primarily eucalyptol.

The oil of citronella is derived from fresh grass of the cymbopogon species with citronellol and geraniol as the primary portions.

The camomile dry mix is cut and sifted first and then lightly milled until it is finely chopped with a tea bag quality. The pennyroyal and eucalyptus are cut and sifted until they are milled in a finely chopped, tea bag quality mix and added to the camomile. The oils of pennyroyal, eucalyptus and citronella are intermixed and lightly sprayed on the dry mix.

The herbal composition consists of between 93% and 99% by weight dry mix and between 1% and 7% by weight oil mix. Furthermore, the dry mix percentage by weight of active dry ingredients varies between 5% and 50% camomile, 5% and 50% pennyroyal, and 5% and 50% eucalyptus. Finally, the oil mix percentage by weight of the oil ingredients varies between 20% and 80% pennyroyal oil, 5% and 40% eucalyptus oil, and 5% and 40% citronella oil. Please note the dry mix percentage and the oil mix percentage are based upon a 100% dry mix and a 100% oil mix.

The preferred herbal composition is made of 32⅔ percent by weight camomile in dry mix, 32⅔ percent by weight pennyroyal in dry mix, and 32⅔ percent by weight eucalyptus in dry mix. 1.2 percent by we pennyroyal oil, 0.4 percent by weight eucalyptus oil and 0.4 percent by weight citronella oil are added to the dry mix of the camomile, pennyroyal, and eucalyptus.

Figure 1:
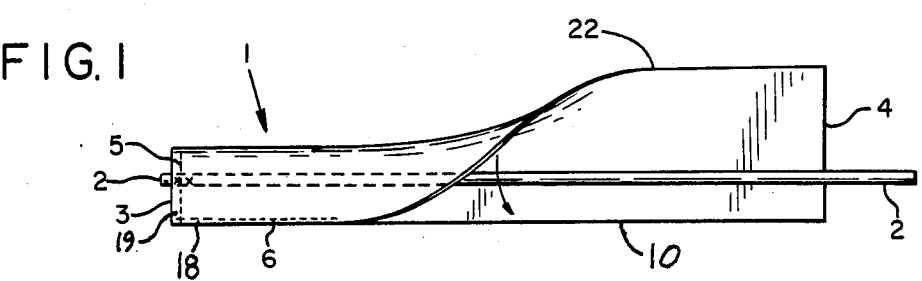
FIG. 1 is a view of the fabric showing the cord stitched to and the beginning of length stitching to form the material receptical.

In FIG. 1, a material receptical 1 is shown with the cord 2. The base stitch 5 has been completed at the material receptical base 3. The length stitch 6 has been partially completed by joining the material receptical upper side 22 to the material receptical lower side 10. The length seam 18 and base seam 19 are visible. The material receptical top 4 is shown.

Figure 2:
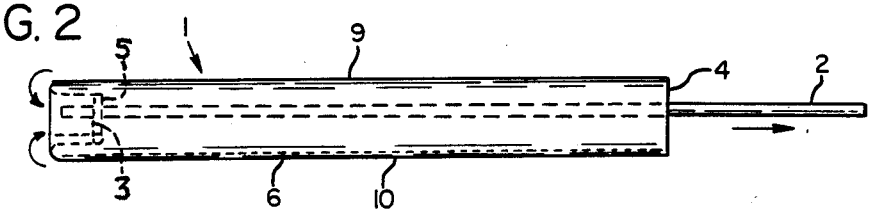
FIG. 2 shows the cord drawing the material receptical right side out.

FIG. 2 shows the cord 2 pulled so as to turn the material receptical 1 right side out so that the base stitch 5, length stitch 6, base seam 19, and length seam 18 become invisible. The material receptical top side 9 is shown completely formed.

Figure 3:
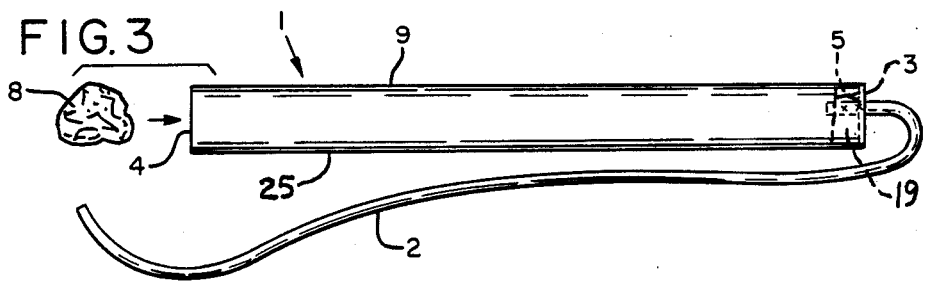
FIG. 3 shows the step of the herbal composition being added to the material receptical.

FIG. 3 represents the herbal composition 8 inserted within the material receptical 1 through the open material receptical top 4. The cord 2 is attached to the material receptical base 3. The material receptical bottom side 25 is now shown.

Figure 4:
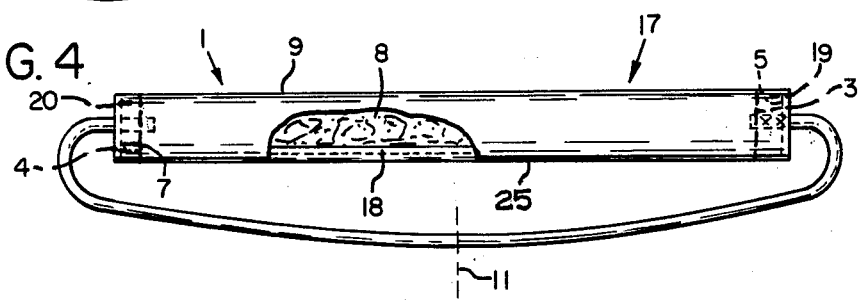
FIG. 4 shows the loose end of the cord and the top of the material receptical stitched together with the herbal composition within the material receptical.

In FIG. 4, herbal composition 8 is within the material receptical 1. The top stitch 7 is completed over the material receptical top 4 and the cord 2 which is divided in half at cut 11. The top seam 20 is not visible. The length stitch 6 and length seam 18 are within the material receptical 1. With cut 11 the pet collar 17 is complete.

Figure 5:
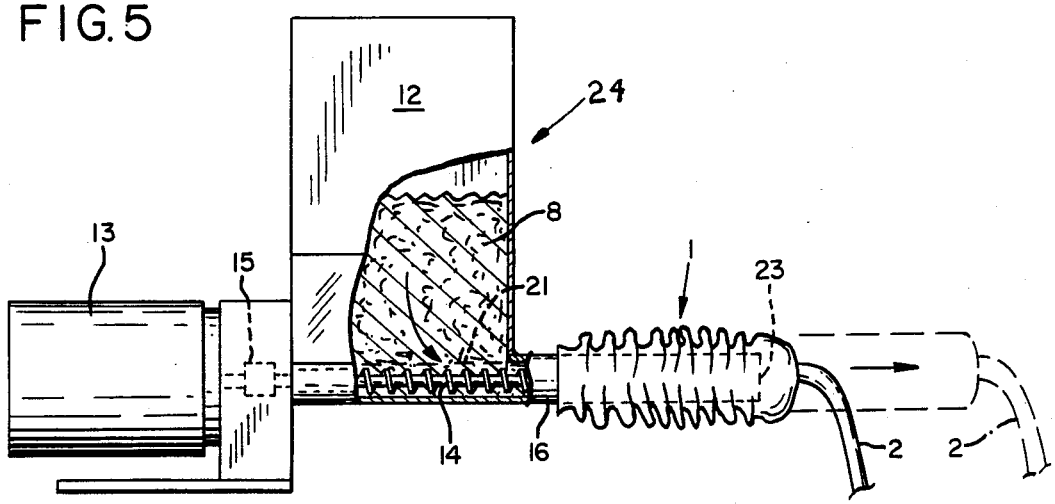
FIG. 5 shows the apparatus adding the herbal composition to the material receptical.

FIG. 5 shows the apparatus 24, with the material receptical 1 placed over the cylinder 16 and cylinder opening 23. The composition 8 is in the hopper 12 and the hopper base 21 commun-icates with the cylinder 16. An auger 14 by means of a coupling 15 is attached to a motor 13.

The material receptical 1 is cut in rectangular form from lengths of closely woven material. The cord 2 is placed in the middle of the lower half of the material receptical 1, lengthwise, with the cord 2 extending about a ¼" past the material receptical base 3. The material receptical upper side 22 is folded over the cord 2 until the material receptical upper side 22 and the material receptical lower side 10 coincide. The material receptical base 3 with the cord 2 is sewed securely closed by the base stitch 5 which traverses the complete distances up and down the base material receptical 3 over the cord 2. The material receptical 1 is then sewn along the material receptical lower side 10 joining it to the material receptical upper side 22 by length stitch 6. The material receptical 1 is then turned right side out by pulling on the cord 2. The base stitch 5, base seam 19, length stitch 6, and length seam 18 are inside of the material receptical 1.

The material receptical top 4 fits completely over the cylinder 16. The material receptical 1 is filled with herbal composition 8 an inch from the material receptical top 4 by the apparatus 24. The material receptical top 4 is folded ⅜" inside the material receptical 1 and about ¾" of the cord 2 is inserted. The top stitch 7 is completed by sewing back and forth until the cord 2 is secure. Thus the top stitch 7 is visible while the material receptical top 4 and top seam 20 are not visible. The cord 2 is severed in the middle at cut 11 so that the ends are of the same length.

In operation, the apparatus 24 is operated by an electrical motor 13. A couple 15 attached to the auger 14 to the motor 13. The herbal composition 8 is placed in the hopper 12 and flows through the hopper base 21 onto the auger 14 but within the cylinder 16. The material receptical top 4 is placed over the cylinder 16. The motor 13 is turned on by the foot switch (not shown) causing the coupler 15 and the auger 14 to rotate. The herbal composition 8 is then transported by the auger 14 into the material receptical base 3 through the cylinder opening 23 which forces the material receptical 1 to slide off of the cylinder 16 during the filling process. Once the material receptical 1 is filled with the herbal composition 8, the motor 13 is stopped.

It will be apparent that various modifications can be made in the particular formulation described in detail. Similarly, various modifications can be made to the method and apparatus. Therefore, the scope of the invention is limited only by the following claims.

What I claim is:

1. An herbal composition comprising active dry ingredients between 93% and 99% by weight consisting of 32⅔% camomile, 32⅔% pennyroyal, and 32⅔% eucalyptus; an active oil ingredients between 1% and 7% by weight consisting of 1.2% pennyroyal oil, 0.4% eucalyptus oil and 0.4% citronella oil.

* * * * *